US009308469B2

(12) United States Patent
Kiuchi et al.

(10) Patent No.: US 9,308,469 B2
(45) Date of Patent: Apr. 12, 2016

(54) DEVICE FOR PRODUCING ETHANOL AND METHOD FOR PRODUCING ETHANOL

(75) Inventors: Takafumi Kiuchi, Fukuoka (JP); Ryohta Hidaka, Fukuoka (JP); Yoichi Ishibashi, Fukuoka (JP); Tomonori Sumi, Fukuoka (JP); Yasuhiko Katoh, Fukuoka (JP); Yasuki Kansha, Tokyo (JP); Atsushi Tsutsumi, Tokyo (JP)

(73) Assignees: NIPPON STEEL & SUMIKIN ENGINEERING CO., LTD., Tokyo (JP); THE UNIVERSITY OF TOKYO, Tokyo (JP)

( * ) Notice: Subject to any disclaimer, the term of this patent is extended or adjusted under 35 U.S.C. 154(b) by 489 days.

(21) Appl. No.: 13/809,269

(22) PCT Filed: Jul. 21, 2011

(86) PCT No.: PCT/JP2011/004119
§ 371 (c)(1),
(2), (4) Date: Apr. 2, 2013

(87) PCT Pub. No.: WO2012/011285
PCT Pub. Date: Jan. 26, 2012

(65) Prior Publication Data
US 2013/0175158 A1 Jul. 11, 2013

(30) Foreign Application Priority Data

Jul. 22, 2010 (JP) .................................. 2010-165151
Apr. 19, 2011 (JP) .................................. 2011-093033

(51) Int. Cl.
*C12P 7/10* (2006.01)
*C12P 7/06* (2006.01)
(Continued)

(52) U.S. Cl.
CPC .............. *B01D 3/143* (2013.01); *C12M 21/12* (2013.01); *C12M 47/10* (2013.01); *C12P 7/06* (2013.01); *C12P 7/10* (2013.01); *Y02E 50/16* (2013.01); *Y02E 50/17* (2013.01)

(58) Field of Classification Search
CPC ......... B01D 3/14; B01D 3/143; C12M 21/12; C12P 7/06; C12P 7/08; C12P 7/10; C12P 7/14; Y02E 50/16
See application file for complete search history.

(56) References Cited

U.S. PATENT DOCUMENTS 4,326,036 A * 4/1982 Hayes ........................... 435/161
4,359,533 A * 11/1982 Wilke et al. .................. 435/161
(Continued)

FOREIGN PATENT DOCUMENTS

CN          1814739        8/2006
JP       2002-345495      12/2002
(Continued)

OTHER PUBLICATIONS

International Search Report issued Sep. 27, 2011 in International (PCT) Application No. PCT/JP2011/004119.
(Continued)

*Primary Examiner* — Brian McCaig
(74) *Attorney, Agent, or Firm* — Wenderoth, Lind & Ponack, L.L.P.

(57) ABSTRACT

Disclosed are a method for producing ethanol and a device for producing ethanol that are suitable to the recycled use of an enzyme.
The device is configured from: a vacuum distillation tower (11) into which an ethanol-fermented liquid generated by saccharification fermentation of a biomass starting material is introduced, and with the interior in a state that is at a lower pressure than atmospheric pressure, that subjects the ethanol-fermented liquid to distillation, distilling ethanol vapor that contains water vapor, and removing as a bottom product the enzyme-containing concentrated waste liquid that is roused for saccharification fermentation of the biomass starting material; and a fractionating tower (12) for fractionating the ethanol vapor distilled from the vacuum distillation tower (11). In this case, the energy of the ethanol vapor can be more efficiently taken advantage of if the device is provided with a first compressor (16) that adiabatically compresses the ethanol vapor distilled from the vacuum distillation tower (11), and the ethanol vapor adiabatically compressed by the first compressor (16) is introduced into the fractionating tower (12).

3 Claims, 6 Drawing Sheets

(51) Int. Cl.
*B01D 3/14* (2006.01)
*C12M 1/00* (2006.01)
*C12P 7/08* (2006.01)
*C12P 7/14* (2006.01)

(56) References Cited

U.S. PATENT DOCUMENTS

2003/0204098 A1* 10/2003 Oka et al. .................. 548/954
2008/0135396 A1 6/2008 Blum

FOREIGN PATENT DOCUMENTS

| | | |
|---|---|---|
| JP | 2005-65695 | 3/2005 |
| JP | 2009-11198 | 1/2009 |
| JP | 2010-17084 | 1/2010 |
| WO | 2007/095875 | 8/2007 |

OTHER PUBLICATIONS

A. Tsutsumi et al., <URL:http://www.energy.iis.u-tokyo.ac.jp/tsutsumi/20100510.pdf#search=Tei Tanso Shakai Kochiku ni Muketa Kakushinteki Engergy Gijutsu>, The University of Tokyo, May 10, 2010.

K. Shiryo, <URL://http://www.energy.iis.u-tokyo.ac.jp/tsutsumi/lecture/html>,The University of Tokyo, May 10, 2010.

International Preliminary Report on Patentability issued Feb. 12, 2013 in International Application No. PCT/JP2011/004119.

Kansha et al., "A New Design Methodology of Azeotropic Distillation Processes Based on Self-Heat Recuperation", Chemical Engineering Transactions, vol. 18, 2009, pp. 51-56.

Matsuda et al., "Advanced energy saving in the reaction section of the hydro-desulfurization process with self-heat recuperation technology", Applied Thermal Engineering, vol. 30, 2010, pp. 2300-2305.

* cited by examiner

US 9,308,469 B2

DEVICE FOR PRODUCING ETHANOL AND METHOD FOR PRODUCING ETHANOL

TECHNICAL FIELD

The present invention relates to an apparatus for producing ethanol and a method for producing ethanol that produce ethanol from a biomass starting material.

BACKGROUND ART

As a convent ional apparatus for producing ethanol, there has been known an apparatus that efficiently utilizes an expensive enzyme by separating, by means of distillation, a reaction liquid of saccharification fermentation from a fermentation product under such a condition as to prevent the deactivation of the enzyme and by performing the recycled use of the enzyme contained in a distillation residual in a saccharification fermentation process and/or a preliminary saccharification process. (See Patent Literature 1, for example).

CITATION LIST

Patent Literature

Patent Literature 1: Japanese Patent Application Laid-open No. 2010-17084

SUMMARY OF INVENTION

Technical Problem

Here in general, when distillation is performed by means of a vacuum distillation tower (or a vacuum concentrating device), it is necessary for the tower bottom temperature to be kept at a temperature higher than or equal to 30° C. and lower than 60° C., preferably in a range of 30° C. or higher and 51° C. or lower, in order to collect an enzyme without causing the deactivation thereof. However, in a case where an energy-saving device such as a multiple-effect evaporator is introduced in order to prevent an excessive evaporation energy, the temperature at the tower top may possibly be below 35° C. Therefore, ethanol vapor under a reduced-pressure condition cannot be condensed with a conventionally-employed cooling tower. Thus, it was necessary to provide a cooler such as a chiller, which consumes a larger amount of power as compared to the cooling tower, and to cool and condense ethanol vapor distilled from the tower top.

Further, when the recycled use of the enzyme is performed, since a liquid amount in a recycling system is increased by an alkaline liquid or a rinse liquid added in a pretreatment process or the like, there is a case where the total amount of an enzyme-containing waste liquid removed as a bottom product from the vacuum distillation tower cannot be returned to a saccharification fermentation device for the reuse thereof.

The present invention has been made in view of such circumstances and is to provide an apparatus for producing ethanol and a method for producing ethanol that are suitable to the recycled use of an enzyme. In particular, an object thereof is to provide an apparatus for producing ethanol and a method for producing ethanol that achieve a reduction in a heat energy and a cooling energy required for the recycled use of an enzyme as compared to a conventional technique.

Moreover, another object of the present invention is to achieve energy conservation in an enzyme-utilizing ethanol production technique by enhancing the energy efficiency of the entire apparatus.

Solution to Problem

An apparatus for producing ethanol according to the first invention satisfying the above-described objects includes: a vacuum distillation tower into which an ethanol-fermented liquid generated by saccharification fermentation of a biomass starting material is introduced, and with an interior in a state that is at a pressure lower than atmospheric pressure, that subjects the ethanol-fermented liquid to distillation, distilling ethanol vapor containing water vapor, and removing as a bottom product an enzyme-containing concentrated waste liquid that is reused for saccharification fermentation of the biomass starting material; and a rectifying column for rectifying the ethanol vapor distilled from the vacuum distillation tower.

The apparatus for producing ethanol according to the first invention may further include a first compressor for adiabatically compressing the ethanol vapor distilled from the vacuum distillation tower, and the ethanol vapor adiabatically compressed by the first compressor may be introduced into the rectifying column.

Also, the apparatus for producing ethanol according to the first invention may further include a first compressor for adiabatically compressing the ethanol vapor distilled from the vacuum distillation tower, and the ethanol vapor adiabatically compressed by the first compressor may be used as a heat source for a heating section for heating a tower bottom recycled liquid for the vacuum distillation tower, then condensed, and introduced into the rectifying column as an ethanol liquid.

In the apparatus for producing ethanol according to the first invention, a bottom temperature of the vacuum distillation tower is preferably a temperature higher than or equal to 30° C. and lower than 60° C.

The apparatus for producing ethanol according to the first invention may further include a first superheater for heating the ethanol vapor distilled from the vacuum distillation tower, the first superheater being provided at a previous stage of the first compressor, and the ethanol vapor heated by the first superheater may be sent to the first compressor so as to prevent condensation thereof in the first compressor.

In the apparatus for producing ethanol according to the to first invention, part of the ethanol vapor adiabatically compressed by the first compressor may be recycled to an entry side of the first compressor.

In the apparatus for producing ethanol according to the is first invention, the ethanol vapor adiabatically compressed by the first compressor may be used as a heat source for the first superheater.

In the apparatus for producing ethanol according to the first invention, a flow rate of the ethanol vapor distilled from the vacuum distillation tower can be adjusted so that a weight of the enzyme-containing concentrated waste liquid to be removed as a bottom product from the vacuum distillation tower becomes 2 to 20 times as much as a pulp weight generated in a pretreatment for enhancing an enzyme reactivity of the biomass starting material.

In the apparatus for producing ethanol according to the first invention, low COD drainage water removed as a bottom product from the rectifying column can be recycled to a pretreatment process for performing a pretreatment for enhancing the enzyme reactivity of the biomass starting material.

In the apparatus for producing ethanol according to the first invention, low COD drainage water removed as a bottom product from the rectifying column can be recycled to a saccharification process for obtaining a monosaccharide by adding a diastatic enzyme to the biomass starting material.

In the apparatus for producing ethanol according to the first invention, low COD drainage water removed as a bottom product from the rectifying column can be recycled as a rinse liquid used in a solid-liquid separation process for separating a solid from the enzyme-containing concentrated waste liquid removed as a bottom product from the vacuum distillation tower.

In the apparatus for producing ethanol according to the first invention, low COD drainage water removed as a bottom product from the rectifying column may be treated by a drainage water treatment apparatus.

In the apparatus for producing ethanol according to the first invention, the low COD drainage water is preferably used as a heat source for the tower bottom recycled liquid for the vacuum distillation tower.

In the apparatus for producing ethanol according to the first invention, the low COD drainage water is preferably further used to preheat the ethanol-fermented liquid.

The apparatus for producing ethanol according to the first invention may preferably further include a second compressor for compressing ethanol vapor distilled from the rectifying column, and part of the ethanol vapor adiabatically compressed by the second compressor is preferably recycled to a top of the rectifying column after being used as a heat source for a heating section that heats a tower bottom recycled liquid for the rectifying column.

In the apparatus for producing ethanol according to the first invention, the low COD drainage water removed as a bottom product from the rectifying column is preferably used as a heat source for preheating the ethanol-fermented liquid and heating the tower bottom recycled liquid for the vacuum distillation tower, and the ethanol vapor compressed by the second compressor is preferably used as a heat source for heating the ethanol liquid to be introduced into the rectifying column.

The apparatus for producing ethanol according to the first invention may further include a second superheater for heating the ethanol vapor distilled from the rectifying column, to the second superheater being provided at a previous stage of the second compressor, and the ethanol vapor heated by the second superheater may be sent to the second compressor.

In the apparatus for producing ethanol according to the first invention, the ethanol vapor adiabatically compressed by the second compressor may be used as a heat source for the second superheater.

In the apparatus for producing ethanol according to the first invention, the enzyme-containing concentrated waste liquid removed as a bottom product from the vacuum distillation tower, the low COD drainage water removed as a bottom product from the rectifying column, and the ethanol vapor distilled from as the rectifying column are preferably used to preheat the ethanol-fermented liquid.

In the apparatus for producing ethanol according to the first invention, a blower or a vacuum pump may be used in place of the first compressor.

In the apparatus for producing ethanol according to the first invention, a blower or a vacuum pump may be used in place of the second compressor.

In the apparatus for producing ethanol according to the first invention, a vacuum concentrating device for concentrating the ethanol-fermented liquid with an interior in a state that is at a pressure lower than atmospheric pressure may be used in place of the vacuum distillation tower.

A method for producing ethanol according to the second invention satisfying the above-described objects is a method for purifying ethanol from an ethanol-fermented liquid generated by saccharification fermentation of a biomass starting material, the method including:

a stop or subjecting the ethanol-fermented liquid to vacuum distillation to produce ethanol vapor that contains water vapor and an enzyme-containing concentrated waste liquid;

a rectifying step for rectifying the ethanol vapor; and a step of recycling the enzyme-containing concentrated waste liquid to a step of subjecting the biomass starting material to saccharification fermentation.

The method for producing ethanol according to the second invention may further include a step of adiabatically compressing the ethanol vapor, and the ethanol vapor having been subjected to temperature increase and pressure increase by the step of adiabatically compressing the ethanol vapor may be introduced into the rectifying step.

The method for producing ethanol according to the second invention may further include a step of adiabatically compressing the ethanol vapor and a step of heat-exchanging the ethanol vapor having been subjected to temperature increase and pressure increase by the step of adiabatically compressing the ethanol vapor with a tower bottom recycled liquid for the vacuum distillation tower to achieve condensation thereof, and the ethanol vapor from the vacuum distillation tower may be introduced into the rectifying step after the ethanol vapor is converted into an ethanol liquid.

Advantageous Effects of Invention

In the apparatus for producing ethanol, vacuum distillation can be performed at a temperature to prevent the deactivation of an enzyme, and the enzyme can be reused. Further, by employing a two-tower system of the vacuum distillation tower and the rectifying column, a degree of freedom for setting an amount of ethanol vapor distillation and an amount of the enzyme-containing concentrated waste liquid removed as a bottom product can be increased as compared to a conventional technique. Thus, the operation thereof becomes possible with the amount of the enzyme-containing concentrated waste liquid removed as a bottom product from the vacuum distillation tower being set to an amount suitable for a flow balance in the enzyme recycling system. Further, the placement of the rectifying column leads to the obtainment of the low COD water, thereby being able to efficiently utilize this water as a rinse liquid.

In the apparatus for producing ethanol, the ethanol vapor adiabatically compressed by the first compressor is introduced into the rectifying column. Thus, since the ethanol vapor is introduced into the rectifying column while being in a state where the temperature and pressure thereof have been increased, it is possible to reduce a consumption energy required in the rectifying process as compared to a conventional technique.

In the apparatus for producing ethanol, the ethanol vapor adiabatically compressed by the first compressor is used as a heat source for the heating section that heats the tower bottom recycled liquid for the vacuum distillation tower, then condensed, and introduced into the rectifying column. Thus, since there is no need to condense the ethanol vapor with a cooler, it is possible to reduce a consumption energy required in the vacuum distillation process and the rectifying process as compared to a conventional technique.

Particularly in the apparatus for producing ethanol, the bottom temperature of the vacuum distillation tower is a temperature higher than or equal to 30° C. and lower than 60° C. regardless of the temperature of the ethanol vapor distilled from the top of the vacuum distillation tower. Thus, the deactivation of the enzyme does not occur, thereby being able to reuse the enzyme.

In the apparatus for producing ethanol, since the ethanol vapor is heated, it is possible to prevent the condensation of the ethanol vapor in the first compressor.

In the apparatus for producing ethanol, since the part of the ethanol vapor adiabatically compressed by the first compressor is recycled to the entry side of the first compressor, it is possible to prevent the condensation of the ethanol vapor in the first compressor.

In the apparatus for producing ethanol, the ethanol vapor adiabatically compressed by the first compressor is used as a heat source for the first superheater. Thus, it is possible to reduce a consumption energy required in the vacuum distillation process as compared to a conventional technique.

In the apparatus for producing ethanol, by providing the rectifying column at the subsequent stage of the vacuum distillation tower, a degree of freedom for setting an amount of ethanol vapor distillation and an amount is of the enzyme-containing concentrated waste liquid removed as a bottom product can be increased as compared to a conventional technique. Thus, it is possible to maintain a preferable liquid balance in the enzyme recycling system by setting the amount removed as a bottom product to 2 to 20 times, preferably 5 to 10 times, as much as the pulp weight generated in the pretreatment for enhancing the enzyme reactivity of the biomass starting material, for example.

In the apparatus for producing ethanol, since water contained in the biomass starting material or water added in the process of producing ethanol can be discharged as the low COD drainage water, it can be reused in the pretreatment process.

In the apparatus for producing ethanol, since water contained in the biomass starting material or water added in the process of producing ethanol can be discharged as the low COD drainage water, it can be reused in the saccharification process.

In the apparatus for producing ethanol, since water contained in the biomass starting material or water added in the process of producing ethanol can be discharged as the low COD drainage water, it can be reused as a rinse liquid used in the solid-liquid separation process.

In the apparatus for producing ethanol, since the drainage water treatment for the low COD drainage water is easily performed, it is possible to reduce a burden of the waste liquid treatment as compared to a conventional technique.

In the apparatus for producing ethanol, the low COD drainage water is used as a heat source for the tower bottom recycled liquid for the vacuum distillation tower. Thus, it is possible to reduce a consumption energy required in the vacuum distillation process as compared to a conventional technique.

In the apparatus for producing ethanol, the low COD drainage water is further used to preheat the ethanol-fermented liquid. Thus, it is possible to reduce a consumption energy required in the vacuum distillation process as compared to a conventional technique.

In the apparatus for producing ethanol, the part of the ethanol vapor adiabatically compressed by the second compressor is recycled to the top of the rectifying column after being used as a heat source for the heating section that heats the tower bottom recycled liquid for the rectifying column. Thus, it is possible to reduce a consumption energy required in the vacuum distillation process and the rectifying process as compared to a conventional technique.

In the apparatus for producing ethanol, the temperature of the ethanol vapor is increased by means of the adiabatic compression of the ethanol vapor by the second compressor so that the latent heat thereof can be reused together with the sensible heat thereof. Thus, it is possible to reduce a consumption energy required in the vacuum distillation process and the rectifying process as compared to a conventional technique.

In the apparatus for producing ethanol, the enzyme-containing concentrated waste liquid removed as a bottom product from the vacuum distillation tower, the low COD drainage water removed as a bottom product from the rectifying column, and the ethanol vapor distilled from the rectifying column are used to preheat the ethanol-fermented to liquid. Thus, it is possible to reduce a consumption energy required in the vacuum distillation process as compared to a conventional technique.

In the apparatus for producing ethanol, the blower or the vacuum pump can be used in place of the first compressor.

In the apparatus for producing ethanol, the blower or the vacuum pump can be used in place of the second compressor.

In the apparatus for producing ethanol, the vacuum concentrating device that concentrates the ethanol-fermented liquid can be used in place of the vacuum distillation tower.

In the method for producing ethanol, by employing a two-stage system of the vacuum distillation and the rectification, the operation thereof becomes possible with the amount of the enzyme-containing concentrated waste liquid generated by the vacuum distillation being set to an amount suitable for the flow balance in the enzyme recycling system.

In the method for producing ethanol, the adiabatically-compressed ethanol vapor is subjected to the rectification while being in a state where the temperature and pressure thereof have being increased. Thus, it is possible to reduce a consumption energy required in the rectifying process as compared to a conventional technique.

In the method for producing ethanol, the adiabatically-compressed ethanol vapor is heat-exchanged with the tower bottom recycled liquid for the vacuum distillation tower, condensed and rectified. Thus, since there is no need to condense the ethanol vapor with a cooler, it is possible to reduce a consumption energy required in the vacuum distillation process and in the rectifying process as compared to a conventional technique.

DESCRIPTION OF EMBODIMENTS

[First Embodiment]

Embodiments embodying the present invention will now be described with reference to the accompanying drawings in order to provide the understanding of the present invention. Note however that the technical scope of the present invention is not limited by the following embodiments.

Figure 1:
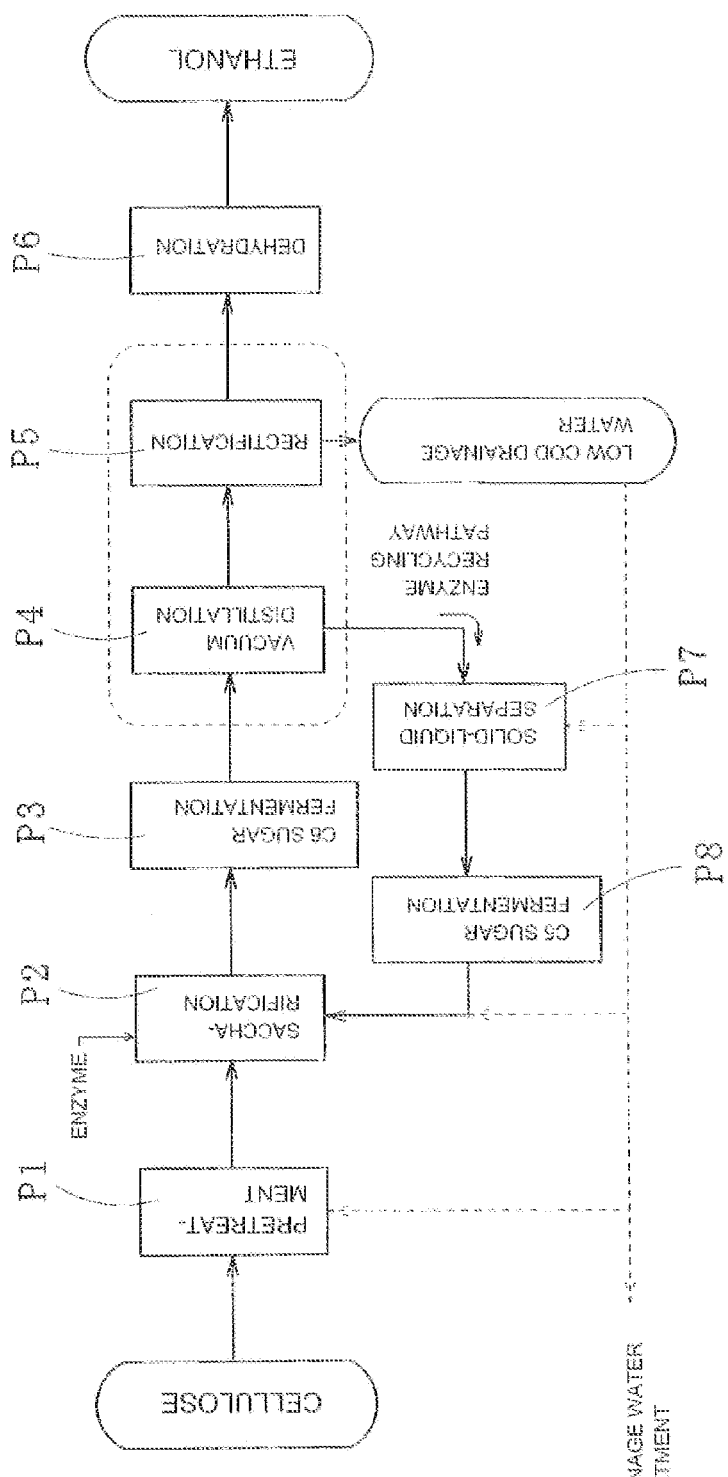
FIG. 1 is a flow diagram of a production process in an apparatus for producing ethanol according to a first embodiment of the present invention.

An apparatus for producing ethanol 10 according to the first embodiment of the present invention (see FIG. 2) produces ethanol from a wood-based, herbaceous, or paper-based biomass starting material containing cellulose. As shown in FIG. 1, an ethanol production process includes a pretreatment process P1, a saccharification process P2, a C6 sugar fermentation process P3, a vacuum distillation process P4, a rectifying process P5, and a dehydration process P6. This production process further includes a solid-liquid separation process P7 and a C5 sugar fermentation process P8.

In the pretreatment process P1, a biomass starting material is subjected to a pretreatment such as a heat treatment, a chemical treatment, or a machine process in order to enhance the enzyme reactivity of the biomass starting material.

In the saccharification process P2, a diastatic enzyme such as cellulase or hemicellulase is added to the pretreated biomass starting material so as to hydrolyze cellulose or the like, thereby obtaining a monosaccharide.

In the C6 sugar fermentation process P3, yeast is added to a saccharified liquid containing the monosaccharide obtained in the saccharification process P2. As a result of the fermentation thereof, an ethanol-fermented liquid is obtained. This ethanol-fermented liquid contains 1 to 10% ethanol. This process may be a simultaneous saccharification and fermentation process (a process performed simultaneously with the saccharification process P2).

In the vacuum distillation process P4, the ethanol-fermented liquid obtained in the C6 sugar fermentation process P3 is distilled so as to separate ethanol therefrom. Specifically, the ethanol-fermented liquid is introduced into a vacuum distillation tower 11 (see FIG. 2), and ethanol is distilled from the top of the tower. The ethanol-fermented liquid to be introduced contains a diastatic enzyme such as cellulase or hemicellulase and the C5 sugar which has not been fermented in the C6 sugar fermentation process P1. Since cellulase or hemicellulase is deactivated at a temperature higher than or equal to 60° C., a bottom temperature of the vacuum distillation tower 11 is adjusted to be lower than that temperature. Since an enzyme is deactivated over time even at a temperature lower than 60°, the bottom temperature of the vacuum distillation tower 11 is preferably as low as possible.

In the rectifying process P5, a low-concentration ethanol-water distilled from the vacuum distillation tower 11 is condensed to about 90%. In the dehydration process P6, water is separated from the ethanol condensed in the rectifying process P5 by means of membrane separation, azeotropy, or the like.

In the solid-liquid separation process, a solid is separated from an enzyme-containing concentrated waste liquid removed as a bottom product from the vacuum distillation tower 11 in the vacuum distillation process P4.

In the C5 sugar fermentation, process P8, the C5 sugar contained in the enzyme-containing concentrated waste liquid from which the solid has been separated is fermented. The fermented liquid is recycled to the saccharification process P2.

Next, the vacuum distillation process P4 and the rectifying process P5 surrounded by a dot line in FIG. 1 will be described in detail.

Figure 2:
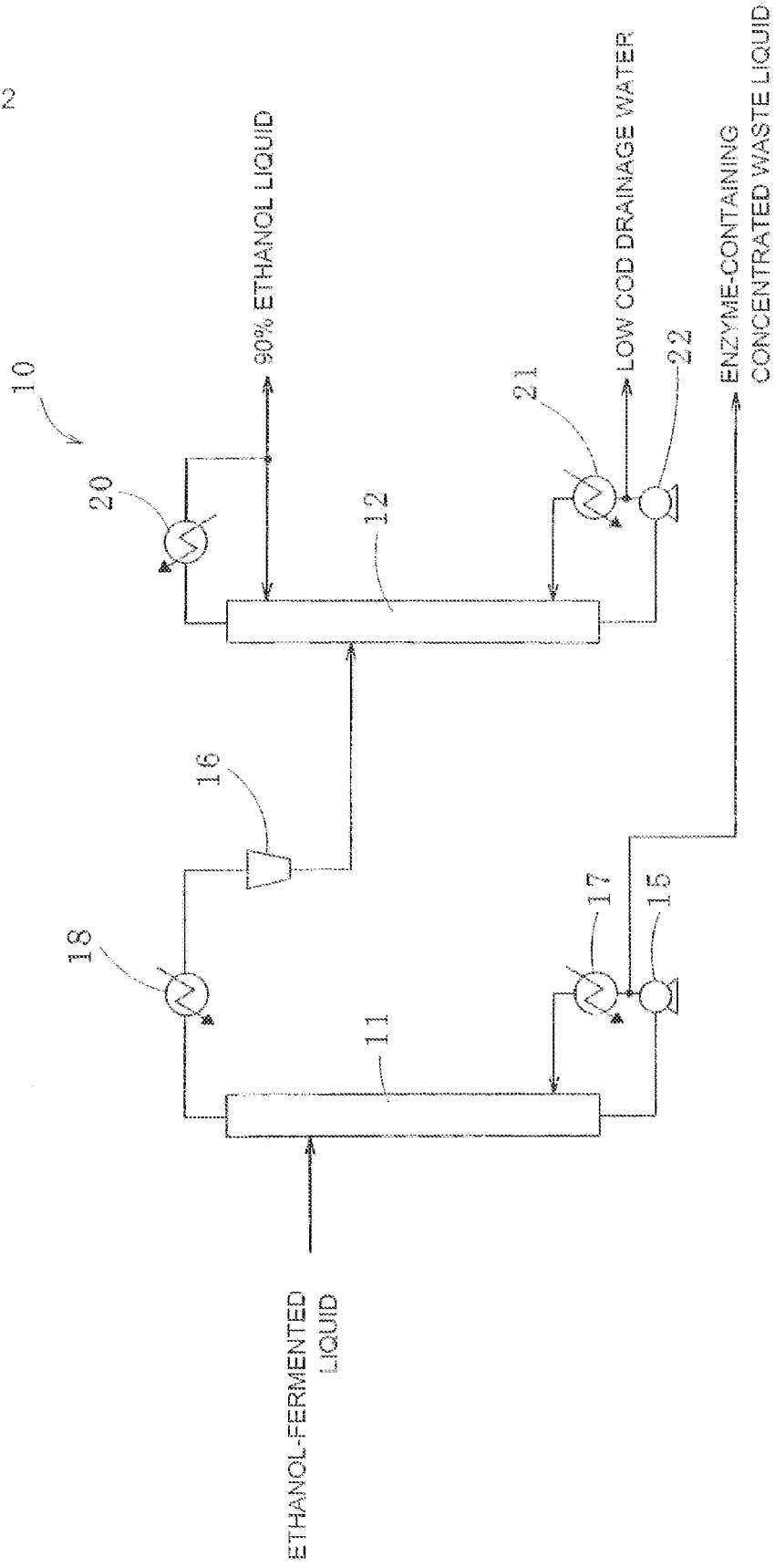
FIG. 2 is a configuration diagram of the apparatus for producing ethanol according to the first embodiment of the present invention.

In these processes, distillation and rectification are performed by the vacuum distillation tower 11 and a rectifying column 12, respectively, as shown in FIG. 2.

The ethanol-fermented liquid generated in the C6 sugar fermentation process P3 is introduced into the vacuum distillation tower 11. A first compressor 16 performs depressurization control for the internal pressure of the vacuum distillation tower 11 so that the bottom temperature thereof becomes a temperature higher than or equal to 30° C. and lower than 60° C. (preferably, in a range of 30° C. or higher and 51° (C or lower). The internal pressure at the top of the vacuum distillation tower 11 is controlled to be 16 kPaA, for example.

The enzyme-containing concentrated waste liquid is removed as a bottom product from the bottom of the vacuum distillation tower 11. The enzyme-containing concentrated waste liquid removed as a bottom product is sent out by a tower bottom recycling pump 15, subjected to the solid-liquid separation process P7, and then reused in a fermenter in the C5 sugar fermentation process P8.

Part of the enzyme-containing concentrated waste liquid, which has been removed as a bottom product from the bottom of is the vacuum distillation tower 11, is subjected to temperature increase by means of a heat exchanger 17 as a tower bottom recycled liquid and then recycled into the bottom of the vacuum distillation tower 11. Note that the heat exchanger 17 employs, as a heat source, vapor fed from a vapor line (not shown). The bottom temperature of the vacuum distillation tower 11 is 45° C., for example.

Moreover, although the heat exchanger 17 is placed outside the vacuum distillation tower 11, it may be integrated with the bottom portion of the vacuum distillation tower 11 so that a heat exchange can be conducted with the vapor fed from the vapor line (not shown).

Ethanol vapor (the temperature thereof is 41° C., for example) is distilled from the top of the vacuum distillation tower 11. Note that an amount of the ethanol-fermented liquid and an amount of the enzyme-containing concentrated waste liquid are predetermined, and a difference therebetween corresponds to an amount of ethanol and water to be distilled. The amount of the enzyme-containing concentrated waste liquid is set to 2 to 20 times (preferably 5 to 10 times, for example, 9 times) as much as the pulp weight generated in the pretreatment process P1 by adjusting a flow rate of the ethanol vapor distilled from the vacuum distillation tower 11. The distilled ethanol vapor is heated by a first superheater 18 so as to prevent the condensation thereof while being delivered to the rectifying column 12. Here in general, if the ethanol vapor distilled from the tower top is condensed while being delivered to the rectifying column 12, a mechanical problem may occur, for example, an excessive load may be imposed on a rotating part such as an impeller (a vane part) within the first compressor 16, the condensed liquid may be leaked from a sealing portion, or the like. In the present embodiment, since the ethanol vapor distilled from the top of the vacuum distillation tower 11 is heated, by the first superheater 18, it is possible to prevent the occurrence of the problem caused by such condensation.

Further, the heated ethanol vapor is adiabatically compressed, and the temperature thereof and the pressure thereof are thus increased by the first compressor 16. Thereafter, the ethanol vapor is introduced into the rectifying column 12.

The ethanol vapor is introduced into the rectifying column 12 as vapor without being cooled and condensed with a chiller or the like as in a conventional technique. Therefore, an energy required for cooling and a heat energy required for the rectifying column 12 are reduced.

Note that the ethanol vapor adiabatically compressed by the first compressor 16 may be introduced into the rectifying column 12 after being used as a heat source for the first superheater 18 provided at the previous stage of the first compressor 16. As a result, it is possible to prevent the condensation of the ethanol vapor in the first compressor 16.

Moreover, without providing the first superheater 18, the condensation of the ethanol vapor in the first compressor 16 may be prevented by recycling part of the ethanol vapor, which has been subjected to the adiabatic compression to increase the temperature and pressure thereof by means of the first compressor 16, to the entry side of the first compressor 16. Further, in a case where there is no possibility of generating the above-described problem due to the condensation, the distilled ethanol vapor may be directly compressed by the first compressor 16 without providing the first superheater 18 at the previous stage of the first compressor 16.

In the rectifying column 12, the introduced ethanol vapor is separated into an ethanol liquid with an ethanol concentration of about 90% and low COD (Chemical Oxygen Demand) drainage water.

The ethanol liquid is distilled from the tower top as ethanol vapor (the temperature thereof is 79° C., for example). The ethanol vapor is cooled at a cooler 20 to be an ethanol liquid and the liquid is then sent to the dehydration process P6. Note that part of the ethanol liquid is recycled to the top of the rectifying column 12 for the purpose of a reflux operation.

The low COD drainage water is removed as a bottom product from the bottom of the rectifying column 12 and then sent out by a tower bottom recycling pump 22. Since this low COD drainage water is a distillate from the vacuum distillation tower 11, it contains no high-boiling component but contains only slight amounts of organic acid, oil, and the like. Therefore, it can be considered as colorless, transparent, and clean water although the COD of the low COD drainage water is about 1000 (mg/L). Thus, the recycled use of the low COD drainage water is possible in the pretreatment process P1, the saccharification process P2, or the solid-liquid separation process P7. Particularly in the solid-liquid separation process P7, the low COD drainage water is used as a rinse liquid. The low COD drainage water can also be treated by a drainage water treatment apparatus (not shown).

Part of the low COD drainage water is subjected to temperature increase by means of a heat exchanger 21 and then recycled to the bottom of the rectifying column 12. As a result, the temperature of the tower bottom is 100° C., for example.

[Second Embodiment]

An apparatus for producing ethanol 200 according to the second embodiment of the present invention will now be described. Note that an ethanol production process thereof is the same as that described in the first embodiment.

Figure 3:
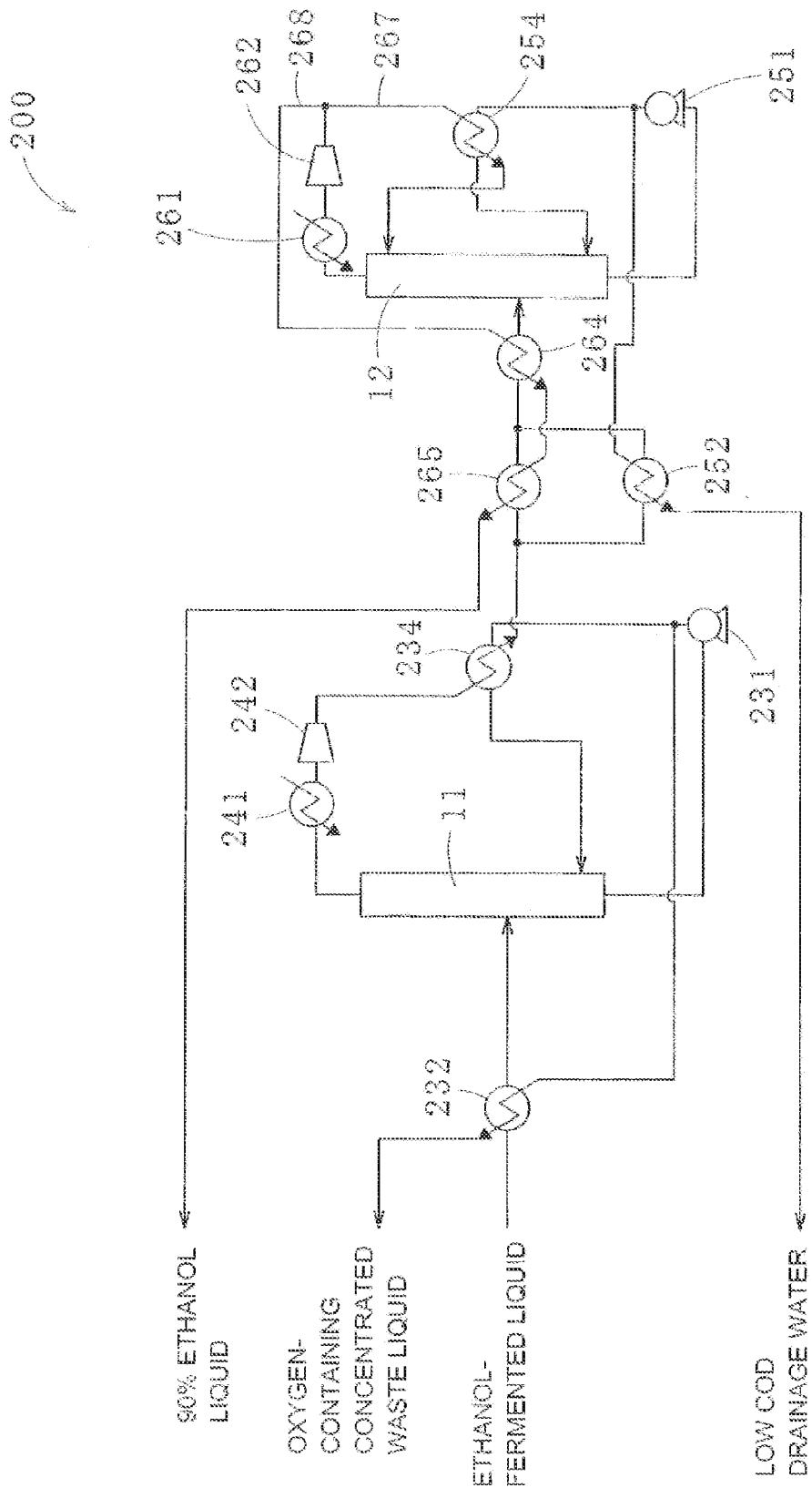
FIG. 3 is a configuration diagram of an apparatus for producing ethanol according to a second embodiment of the to present invention.

As shown in FIG. 3, in the vacuum distillation process P4 and the rectifying process P5 of the apparatus for producing ethanol 200, distillation and rectification are performed by the vacuum distillation tower 11 and the rectifying column 12, respectively.

The ethanol-fermented liquid generated in the C6 sugar fermentation process P3 is introduced into the vacuum distillation tower 11. In order to prevent the deactivation of the diastatic enzyme, a first compressor 242 performs depressurization control so that the bottom temperature of the vacuum distillation tower 11 becomes a temperature higher than or equal to 30° C. and lower than 60° C. (preferably, in a range of 30° C. or higher and 51° C. or lower). The internal pressure at the top of the vacuum distillation tower 11 is controlled to be 16 kPaA, for example.

The enzyme-containing concentrated waste liquid is removed as a bottom product from the bottom of the vacuum distillation tower 11. The enzyme-containing concentrated waste liquid removed as a bottom product is sent out by a tower bottom recycling pump 231, subjected to the solid-liquid separation process P7, and then reused in the fermenter in the C5 sugar fermentation process P8. Moreover, the enzyme-containing concentrated waste liquid preheats the ethanol-fermented liquid by means of a preheater 232.

Part of the enzyme-containing concentrated waste liquid, which has been removed as a bottom product from the bottom of the vacuum distillation tower 11, is subjected to heat input and temperature increase by means of a heat exchanger (heating section) 234 and then recycled into the bottom of the vacuum distillation tower 11 as a tower bottom recycled liquid.

Note that the heat exchanger 234 employs, as a heat source, ethanol vapor having been distilled from the top of the vacuum distillation tower 11 and subjected to temperature increase by the adiabatic compression by means of the first compressor 242. The bottom temperature of the vacuum distillation tower 11 is 45° C., for example. Moreover, although the heat exchanger 234 is placed outside the vacuum distillation tower 11, it may be integrated with the bottom portion of the vacuum distillation tower 11 so that a heat exchange can be conducted with vapor fed from the vapor line (not shown).

Ethanol vapor (the temperature thereof is 41° C., for example) is distilled from the top of the vacuum distillation tower 11. Note that since an amount of the ethanol-fermented liquid and an amount of the enzyme-containing concentrated waste liquid are predetermined, a difference therebetween corresponds to an amount of ethanol and water to be distilled. The amount of the enzyme-containing concentrated waste liquid is set to 2 to 20 times (preferably 5 to 10 times, for example, 9 times) as much as the pulp weight generated in the pretreatment process P1 by adjusting a flow rate of the ethanol vapor distilled from the vacuum distillation tower 11. The following methods, for example, can be conceived in order to control the recycled amount of the enzyme-containing concentrated waste liquid. As a first example, in order to maintain a fixed level in a buffer tank of a C5 sugar-fermented liquid, the control therefor can be made by altering a supplied amount of vapor in the vacuum distillation process P4, the number of revolutions in the first compressor 242, or an amount of the ethanol vapor distilled from the vacuum distillation tower 11. As a second example, refractivity (sugar concentration) of the enzyme-containing concentrated waste liquid is measured by means of a refractometer (Brix meter). In order to maintain this measured value constant, the control therefor can be made by altering a supplied amount of vapor in the vacuum distillation process P4, the number of revolutions in the first compressor 242, or an amount of the ethanol vapor distilled from the vacuum distillation tower 11.

The ethanol vapor distilled from the top of the vacuum distillation tower 11 is heated by a first superheater 241 so as to prevent the condensation thereof in the first compressor 242. Here in general, if the ethanol vapor distilled from the tower top is condensed while being delivered to the rectifying column 12, a mechanical problem may occur, for example, an excessive load may be imposed on a rotating part such as an impeller (a vane part) within the first compressor 242, the condensed liquid may be leaked from a sealing portion, or the like. In the present embodiment, since the ethanol vapor distilled from the top of the vacuum distillation tower 11 is heated by the first superheater 241, it is possible to prevent the occurrence of the problem caused by such condensation.

Further, the heated ethanol vapor is adiabatically compressed, and the temperature thereof and the pressure thereof are thus increased by the first compressor 242. Thereafter, the ethanol vapor is heat-exchanged with the enzyme-containing concentrated waste liquid at the bottom of the vacuum distillation tower 11 (tower bottom recycled 11 quid) at the heat exchanger 234 and thus condensed.

Note that the ethanol vapor adiabatically compressed by the first compressor 242 may be introduced into the heat exchanger 234 after being used as a heat source for the first superheater 241 provided at the previous stage of the first compressor 242. As a result, it is possible to prevent the condensation of the ethanol vapor in the first compressor 242. It is also possible to further reduce a consumption energy required in the vacuum distillation process P4. Moreover, without providing the first superheater 241, the condensation of the ethanol vapor in the first compressor 242 may be prevented by recycling part of the ethanol vapor, which has been subjected to the adiabatic compression to increase the temperature and pressure thereof by means of the first compressor 242, to the entry side of the first compressor 242. Further, in a case where there is no possibility of generating the above-described problem due to the condensation, the distilled ethanol vapor may be directly compressed by the first compressor 242 without providing the first superheater 241 at the previous stage of the first compressor 242.

The distilled ethanol liquid from the vacuum distillation tower 11, which has been condensed by the heat exchanger 234, is subjected to temperature increase by means of a preheater 265, a preheater 252, and a preheater 264 and then introduced into the rectifying column 12.

The preheater 265 employs, as a heat source, the ethanol vapor having been distilled from the top of the rectifying column 12, subjected to temperature increase and pressure increase by means of a second compressor 262, sent out through a distillation line 268, and heat-exchanged at the preheater 264 to be a condensed ethanol liquid.

The preheater 252 employs, as a heat source, low COD drainage water removed as a bottom product from the bottom of the rectifying column 12.

The preheater 264 employs, as a heat source, the ethanol vapor having been distilled from the top of the rectifying column 12, subjected to temperature increase and pressure increase by means of the second compressor 262, and sent out through the distillation line 268.

Thus, since the ethanol vapor having been distilled from the top of the vacuum distillation tower 11 and subjected to temperature increase and pressure increase by the first compressor 242 is used as a heat source necessary for operating the vacuum distillation tower 11, there is no need to use an external heat energy such as vapor as in the conventional technique. Thus, an energy required for the operation of the vacuum distillation tower 11 is reduced substantially. Moreover, since the sensible heat of the ethanol distilled liquid and the bottom product liquid from the bottom of the distillation tower is also utilized at the preheaters or the like, the amount of energy use is reduced. Further, the introduction of an energy-saving device such as a multiple-effect evaporator necessitates a cooler such as a chiller, which consumes a larger amount of power as compared to the other devices, if the temperature at the tower top is lower than or equal to 35° C., for example. However, since there is no need to condense the ethanol vapor in the present process, is such a device can be eliminated.

The distilled ethanol liquid to be introduced into the rectifying column 12 is an ethanol liquid with an ethanol concentration of about 10% (10% ethanol liquid). This 10% ethanol liquid is separated at the rectifying column 12 into an ethanol liquid with an ethanol concentration of about 90% and low COD drainage water.

The 90% ethanol liquid is distilled from the top of the rectifying column 12 as ethanol vapor (90% ethanol vapor), heated by a second superheater 261, subjected to temperature increase and pressure increase by the second compressor 262, sent out to the distillation line 268, passed through the preheater 264 and the preheater 265, and sent to the dehydration process P6.

Note that the 90% ethanol vapor preheats, by the preheater 264, the 10% ethanol liquid distilled from the vacuum distillation tower 11 as described above. Moreover, after being condensed at the preheater 264, the 90% ethanol vapor preheats the 10% ethanol liquid by the preheater 265.

Part of the ethanol vapor having been compressed to increase the temperature and pressure thereof by the second compressor 262 is sent out to a reflux line 267. Thereafter, the ethanol vapor sent out to the reflux line 267 is passed through a heat exchanger 254, which is a heating section for the bottom of the rectifying column 12, so as to be heat-exchanged with the tower bottom recycled liquid. As a result, a majority thereof is condensed. The condensed ethanol is recycled to the top of the rectifying column 12 as an ethanol reflux liquid.

Note that the ethanol vapor adiabatically compressed by the second compressor 262 may be sent out to the distillation line 268 and the ref lux line 267 after being used as a heat source for the second superheater 261 provided at the previous stage of the second compressor 262. As a result, it is possible to prevent the condensation of the ethanol vapor in the second compressor 262. It is also possible to further reduce a consumption energy required in the vacuum distillation process P4.

The low COD drainage water is removed as a bottom product from the bottom of the rectifying column 12. Since this low COD drainage water is a distillate from the vacuum distillation tower 11, it contains no high-boiling component but contains only slight amounts of organic acid, oil, and the like. Therefore, it can be considered as colorless, transparent, and clean water although the COD of the low COD drainage water is about 1000 (mg/L). Thus, the recycled use of the low COD drainage water is possible in the pretreatment process P1, the saccharification process P2, or the solid-liquid separation process P7. Particularly in the solid-liquid separation process P7, the low COD drainage water is used as a rinse liquid. The low COD drainage water can also be treated by a drainage water treatment apparatus (not shown).

The low COD drainage water is sent out by a tower bottom recycling pump 251, and preheats the 10% ethanol liquid to be introduced into the rectifying column 12 via the preheater 252 as described above.

Part of the low COD drainage water is subjected to temperature increase by means of the heat exchanger 254 and recycled to the bottom of the rectifying column 12 as a tower bottom recycled liquid. Note that the heat source for the heat exchanger 254 is the ethanol vapor having been compressed to increase the temperature and pressure thereof by means of the second compressor 262. Accordingly, the temperature at the tower bottom is 100° C., for example.

Although the ethanol-fermented liquid is heat-exchanged with the preheater 232, this preheater 232 can be omitted. Moreover, although branched lines (the reflux line 267 and the distillation line 268) for the ethanol vapor distilled from the top of the rectifying column 12 are provided at an exit side of the second compressor 262, the distillation line 268 may alternatively be branched at an entry side of the second compressor 262.

It is also possible to provide a buffer tank for temporarily retaining the condensed ethanol between the heat exchanger 234 and the preheaters 252 and 265.

[Third Embodiment]

An apparatus for producing ethanol 30 according to the third embodiment of the present invention will now be described. Note that an ethanol production process thereof is the same as as that described in the first embodiment.

Figure 4:
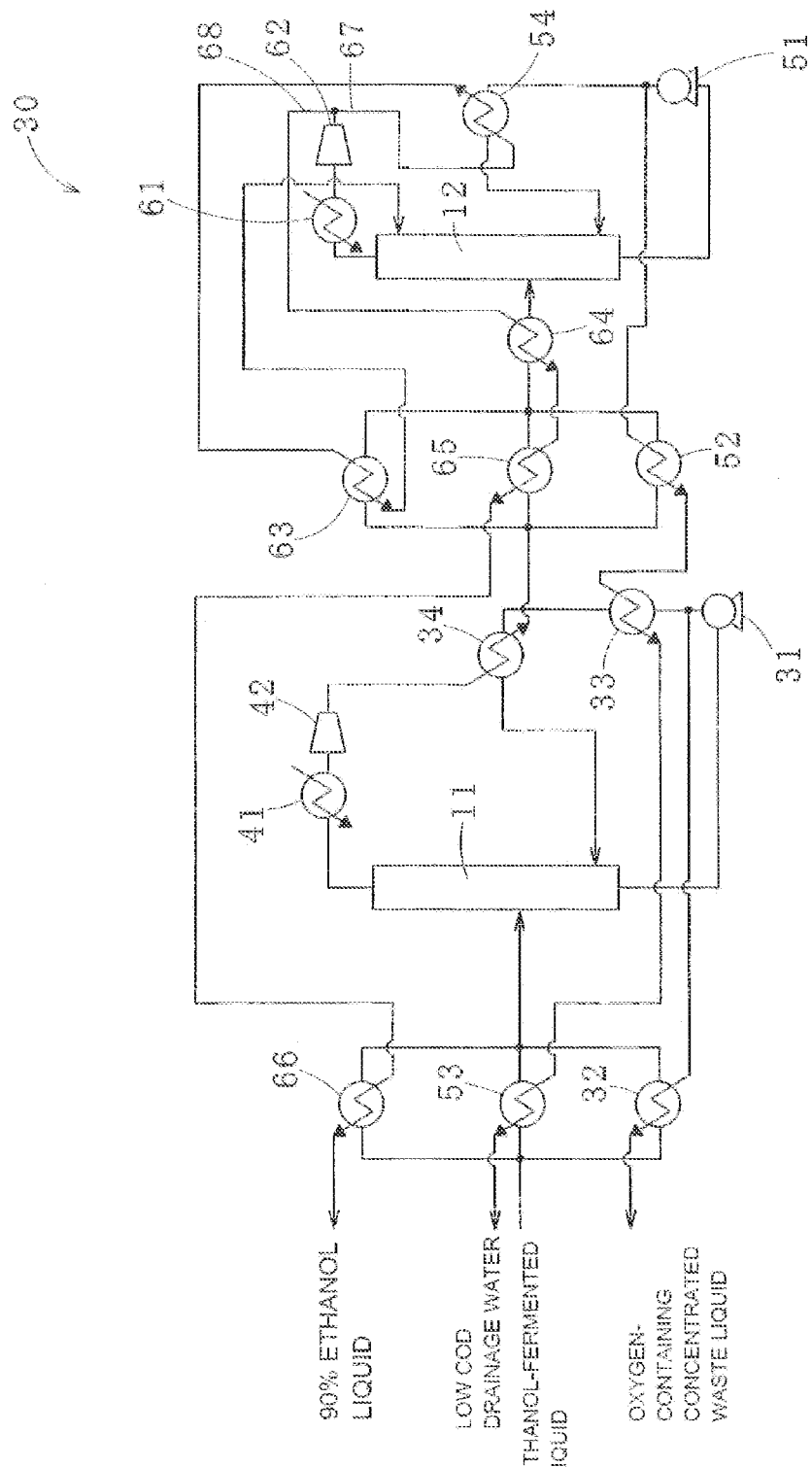
FIG. 4 is a configuration diagram of an apparatus for producing ethanol according to a third embodiment of the present invention.

As shown in FIG. 4, in the vacuum distillation process P4 and the rectifying process P5 of the apparatus for producing ethanol 30, distillation and rectification are performed by the vacuum distillation tower 11 and the rectifying column 12, respectively.

The ethanol-fermented liquid generated in the C6 sugar fermentation process P3 is introduced into the vacuum distillation tower 11. In order to prevent the deactivation of the diastatic enzyme, a first compressor 42 performs depressurization control so that the bottom temperature of the vacuum distillation tower 13 becomes a temperature higher than or equal to 30° C. and lower than 60° C. (preferably, in a range of 30° C. or higher and 51° C. or lower). The internal pressure at the top of the vacuum distillation tower 11 is controlled to be 16 kPaA, for example.

The enzyme-containing concentrated waste liquid is removed as a bottom product from the bottom of the vacuum distillation tower 11. The enzyme-containing concentrated waste liquid removed as a bottom product is sent out by a tower bottom recycling pump 31, subjected to the solid-liquid separation process P7, and then reused in the fermenter in the C5 sugar fermentation process P8. Moreover, the enzyme-containing concentrated waste liquid preheats the ethanol-fermented liquid by means of a preheater 32.

Part of the enzyme-containing concentrated waste liquid, which has been removed as a bottom product from the bottom of the vacuum distillation tower 11, is subjected to heat input and temperature increase by means of a heat exchanger 33 and a heat exchanger 34 (heating sections) and then recycled into the bottom of the vacuum distillation tower 11 as a tower bottom recycled liquid. Note that the heat exchanger 33 employs, as a heat source, low COD drainage water removed as a bottom product from the bottom of the rectifying column 12. The heat exchanger 34 employs, as a heat source, ethanol vapor having been distilled from the top of the vacuum distillation tower 11 and subjected to temperature increase by the adiabatic compression by means of the first compressor 42. The bottom temperature of the vacuum distillation tower 11 is 45° C., for example.

Moreover, although the heat exchanger 33 and the heat exchanger 34 are placed outside the vacuum distillation tower 11, they may be integrated with the bottom portion of the vacuum distillation tower 11 so that a heat exchange can be conducted with vapor fed from a vapor line (not shown).

Ethanol vapor (the temperature thereof is 41° C., for example) is distilled from the top of the vacuum distillation tower 11. Note that an amount of the ethanol-fermented liquid and an amount of the enzyme-containing concentrated waste liquid are predetermined, and a difference therebetween corresponds to an amount of ethanol and water to be distilled. The amount of the enzyme-containing concentrated waste liquid is set to 2 to 20 times (preferably 5 to 10 times, for example, 9 times) as much as the pulp weight generated in the pretreatment process P1 by adjusting a flow rate of the ethanol vapor distilled from the vacuum distillation tower 11. The following methods, for example, can be conceived in order to control the recycled amount of the enzyme-containing concentrated waste liquid. As a first example, in order to maintain a fixed level in a buffer tank of a C5 sugar-fermented liquid, the control therefor can be made by altering a supplied amount of vapor in the vacuum distillation process P4, the number of revolutions in the first compressor 42, or an amount of the ethanol vapor distilled from the vacuum distillation tower 11. As a second example, refractivity (sugar concentration) of the enzyme-containing concentrated waste liquid is measured by means of a refractometer (Brix meter). In order to maintain this measured value constant, the control therefor can be made by altering a supplied amount of vapor in the vacuum distillation process P4, the number of revolutions in the first compressor 42, or an amount of the ethanol vapor distilled from the vacuum distillation tower 11.

The ethanol vapor distilled from the top of the vacuum distillation tower 11 is heated by a first superheater 41 so as to prevent the condensation thereof in the first compressor 42. Here in general, if the ethanol vapor distilled from the tower top is condensed while being delivered to the rectifying column 12, a mechanical problem may occur, for example, an excessive load may be imposed on a rotating part such as an impeller (a vane part) within the first compressor 42, the condensed liquid may be leaked from a sealing portion, or the like. In the present embodiment, since the ethanol vapor distilled from the top of the vacuum distillation tower 11 is heated by the first superheater 41, it is possible to prevent the occurrence of the problem caused by such condensation.

Further, the heated ethanol vapor is adiabatically compressed, and the temperature thereof and the pressure thereof are thus increased by the first compressor 42. Thereafter, the ethanol vapor is heat-exchanged with the enzyme-containing concentrated waste liquid at the bottom of the vacuum distillation tower 11 (tower bottom recycled liquid) by the heat exchanger 34 and thus condensed.

Note that the ethanol vapor adiabatically compressed by the first compressor 42 may be introduced into the heat exchanger 34 after being used as a heat source for the first superheater 41 provided at the previous stage of the first compressor 42. As a result, it is possible to prevent the condensation of the ethanol vapor in the first compressor 42. It is also possible to further reduce a consumption energy required in the vacuum distillation process P4. Moreover, without providing the first superheater 41, the condensation of the ethanol vapor in the first compressor 42 may be prevented by recycling part of the ethanol vapor, which has been subjected to the adiabatic compression to increase the temperature and pressure thereof by means of the first compressor 42, to the entry side of the first compressor 42. Further, in a case where there is no possibility of generating the above-described problem due to the condensation, the distilled ethanol vapor may be directly compressed by the first compressor 42 without providing the first superheater 41 at the previous stage of the first compressor 42.

The distilled ethanol liquid from the vacuum distillation tower 11, which has been condensed by the heat exchanger 34, is subjected to temperature increase by means of a preheater 63, a preheater 65, a preheater 52, and a preheater 64 and then introduced into the rectifying column 12.

The preheater 63 employs, as a heat source, an ethanol liquid obtained by being distilled from the top of the rectifying column 12, subjected to temperature increase and pressure increase by means of a second compressor 62, sent out through a reflux line 67, and heat-exchanged at a heat exchanger 54, which is a heating section for the bottom of the rectifying column 12, to be condensed. The ethanol liquid in the ref ux line 67 partially exists as vapor.

The preheater 65 employs, as a heat source, the ethanol vapor having been distilled from the top of the rectifying column 12, subjected to temperature increase and pressure increase by means of the second compressor 62, sent out through a distillation line 68, and heat-exchanged at the preheater 64 to be a condensed ethanol liquid.

The preheater 52 employs, as a heat source, low COD drainage water removed as a bottom product from the bottom of the rectifying column 12.

The preheater 64 employs, as a heat source, the ethanol vapor having been distilled from the top of the rectifying column 12, subjected to temperature increase and pressure increase by means of the second compressor 62, and sent out through the distillation line 68.

Thus, since the ethanol vapor having been distilled from the top of the vacuum distillation tower 11 and subjected to temperature increase and pressure increase by the first compressor 42 is used as a heat source necessary for operating the vacuum distillation tower 11, there is no need to use an external heat energy such as vapor as in the conventional technique. Thus, an energy required for the operation of the vacuum distillation tower 11 is reduced substantially. Moreover, since the sensible heat of the ethanol distilled liquid and the bottom product liquid from the bottom of the distillation tower is also utilized at the preheaters or the like, the amount of energy use is reduced. Further, the introduction of an energy-saving device such as a multiple-effect evaporator necessitates a cooler such as a chiller, which consumes a larger amount of power as compared to the other devices, if the temperature at the tower top is lower than or equal to 35° C., for example. However, since there is no need to condense the ethanol vapor in the present process, such a device can be eliminated.

The distilled ethanol liquid introduced into the rectifying column 12 is an ethanol liquid with an ethanol concentration of about 10% (10% ethanol liquid). This 10% ethanol liquid is separated at the rectifying column 12 into an ethanol liquid with an ethanol concentration of about 90% and low COD drainage water.

The 90% ethanol liquid is distilled from the top of the rectifying column 12 as ethanol vapor (90% ethanol vapor), heated by a second superheater 61, subjected to temperature increase and pressure increase by the second compressor 62, and then sent out to the distillation line 68. The ethanol vapor sent out to the distillation line 68 is passed through the preheater 64, the preheater 65, and a preheater 66, and sent to the dehydration process P6.

Note that the 90% ethanol vapor preheats, by the preheater 64, the 10% ethanol liquid distilled from the vacuum distillation tower 11 as described above. Moreover, after being condensed at the preheater 64, the 90% ethanol vapor preheats the 1.0% ethanol liquid by the preheater 65.

Part of the ethanol vapor having been compressed to increase the temperature and pressure thereof by the second compressor 62 is sent out to the reflux line 67. Thereafter, the ethanol vapor sent out to the ref lux line 67 is passed through the heat exchanger 54 so as to be heat-exchanged with the tower bottom recycled liquid. As a result, a majority thereof is condensed. The condensed ethanol preheats the 10% ethanol to be introduced into the rectifying column 12 through the preheater 63 and is recycled to the tower top as an ethanol ref lux liquid.

Note that the ethanol vapor adiabatically compressed by the second compressor 62 may be sent out to the distillation line 68 and the reflux line 67 after being used as a heat source for the second superheater 61 provided at the previous stage of the second compressor 62. As a result, it is possible to prevent the condensation of the ethanol vapor in the second compressor 62. It is also possible to further reduce a consumption energy required in the vacuum distillation process P4.

The low COD drainage water is removed as a bottom product from the bottom of the rectifying column 12. Since this low COD drainage water is a distillate from the vacuum distillation tower 11, it contains no high-boiling component but contains only slight amounts of organic acid, oil, and the like. Therefore, it can be considered as colorless, transparent, and clean water although the COD of the low COD drainage water is about 1000 (mg/L). Thus, the recycled use of the low COD drainage water is possible in the pretreatment process P1, the saccharification process P2, or the solid-liquid separation process P7. Particularly in the solid-liquid separation process P7, the low COD drainage water is used as a rinse liquid. The low COD drainage water can also be treated by a drainage water treatment apparatus (not shown).

The low COD drainage water is sent out by a tower bottom recycling pump 51. The low COD drainage water preheats the 10% ethanol liquid to be introduced into the rectifying column 12 via the preheater 52 as described above, and is heat-exchanged with the tower bottom recycled liquid of the vacuum distillation tower 11 by the heat exchanger 33. The low COD drainage water also preheats the ethanol-fermented liquid by a preheater 53.

Part of the low COD drainage water is subjected to temperature increase by means of the heat exchanger 54 and recycled to the bottom of the rectifying column 12. Note that the heat source for the heat exchanger 54 is the ethanol vapor having been compressed to increase the temperature and pressure thereof by means of the second compressor 62 as described above. Accordingly, the temperature at the tower bottom is 100° C., for example.

Although the heat exchange of the ethanol-fermented liquid is performed by the preheater 32, the preheater 53, and the preheater 66 arranged in parallel, these preheaters 32, 53, and 66 may be serially arranged or omitted in a case where the cost required for the branch of the ethanol-fermented liquid becomes excessive, or the like. Moreover, although branched lines (the reflux line 67 and the distillation line 68) for the ethanol vapor distil led from the top of the rectifying column 12 are provided at an exit side of the second compressor 62, the distillation line 68 may alternatively be branched at an entry side of the second compressor 62.

[Fourth Embodiment]

An apparatus for producing ethanol 70 according to the fourth embodiment of the present invention will now be described. Note that an ethanol production process thereof is the same as that described in the first embodiment.

Figure 5:
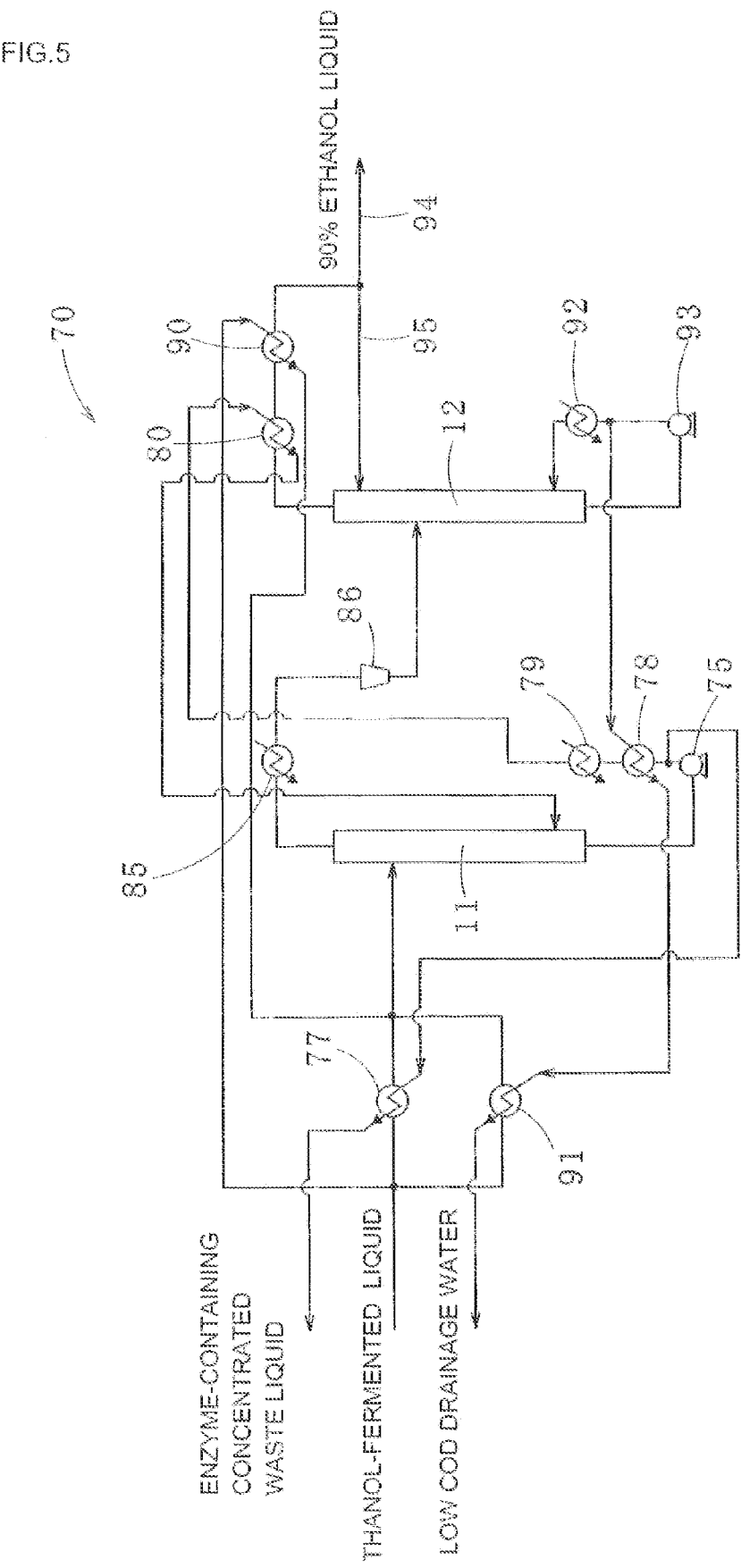
FIG. 5 is a configuration diagram of an apparatus for producing ethanol according to a fourth embodiment of the present invention.

As shown in FIG. 5, in the vacuum distillation process P4 and the rectifying process P5 of the apparatus for producing ethanol 70, distillation and rectification are performed by the vacuum distillation tower 11 and the rectifying column 12, respectively.

The ethanol-fermented liquid generated in the C6 sugar fermentation process P3 is introduced into the vacuum distillation tower 11. In order to prevent the deactivation of the diastatic enzyme, a first compressor 86 performs depressurization control so that the bottom temperature of the vacuum distillation tower 11 becomes a temperature higher than or equal to 30° C. and lower than 60° C. (preferably, in a range of 30° C. or higher and 51° C. or lower). The internal pressure of the vacuum distillation tower 11 is controlled to be 16 kPaA, for example.

The enzyme-containing concentrated waste liquid is removed as a bottom product from the bottom of the vacuum distillation tower 11. The enzyme containing concentrated waste liquid removed as a bottom product is sent out by a tower bottom recycling pump 75, subjected to the solid-liquid separation process P7, and then reused in the fermenter in the C5 sugar fermentation process P8. Moreover, the enzyme-containing concentrated waste liquid preheats the ethanol-fermented liquid by mains of a preheater 77.

The enzyme-containing concentrated waste liquid from the bottom of the vacuum distillation tower 11 is subjected to temperature increase by means of a heat exchanger 78, a heat exchanger 79, and a heat exchanger 80 and then recycled into the bottom of the vacuum distillation tower 11 as a tower bottom recycled liquid. Note that the heat exchanger 78 employs, as a heat source, low COD drainage water (the temperature thereof is 100° C., for example) removed as a bottom product from the bottom of the rectifying column 12. The heat exchanger 79 performs a heat exchange with external vapor fed from a vapor line (not shown). The heat exchanger 80 performs a heat exchange with the ethanol vapor distilled from the top of the rectifying column 12. The bottom temperature of the vacuum distillation tower 11 is 45° C., for example.

Moreover, although the heat exchanger 78 and the heat exchanger 79 are placed outside the vacuum distillation tower 11, they may be integrated with the bottom portion of the vacuum distillation tower 11 so that a heat exchange can be conducted with vapor fed from the vapor line (not shown).

Ethanol vapor (the temperature thereof is 41° C., for example) is distilled from the top of the vacuum distillation tower 11. Note that an amount of the ethanol-fermented liquid and an amount of the enzyme-containing concentrated waste liquid are predetermined, and a difference therebetween corresponds to an amount of ethanol and water to be distilled. The amount of the enzyme-containing concentrated waste liquid is set to 2 to 20 times (preferably 5 to 10 times, for example, 9 times) as much as the pulp weight generated in the pretreatment process P1 by adjusting a flow rate of the ethanol vapor distilled from the vacuum distillation tower 11. The following methods, for example, can be conceived in order to control the recycled amount of the enzyme-containing concentrated waste liquid. As a first example, in order to maintain a fixed level to in a buffer tank of a C5 sugar-fermented liquid, the control therefor can be made by altering a supplied amount of vapor in the vacuum distillation process P4, the number of revolutions in the first compressor 86, or an amount of the ethanol vapor distilled from the vacuum distillation tower 11. As a second example, refractivity (sugar concentration) of the enzyme-containing concentrated waste liquid is measured by means of a refractometer (Brix meter). In order to maintain this measured value constant, the control therefor can be made by altering a supplied amount of vapor in the vacuum distillation process P4, the number of revolutions in the first compressor 86, or an amount of the ethanol vapor distilled from the vacuum distillation tower 11.

The ethanol vapor distilled from the top of the vacuum distillation tower 11 is heated by a first superheater 85 so as to prevent the condensation thereof while being delivered to the rectifying column 12. Here in general, if the ethanol vapor distilled from the tower top is condensed while being delivered to the rectifying column 12, a mechanical problem may occur, for example, an excessive load may be imposed on a rotating part such as an impeller (a vane part) within the first compressor 86, the condensed liquid may be leaked from a sealing portion, or the like. In the present embodiment, since the ethanol vapor distilled from the top of the vacuum distillation tower 11 is heated by the first superheater 85, it is possible to prevent the occurrence of the problem caused by such condensation.

Further, the heated ethanol vapor is adiabatically compressed, and the temperature thereof and the pressure thereof are thus increased by the first compressor 86. Thereafter, the ethanol vapor is introduced into the rectifying column 12.

Thus, since the ethanol vapor is introduced into the rectifying column 12 as vapor without being cooled and condensed as in a conventional technique, an energy required for the operation of the rectifying column 12 is substantially reduced. Further, the introduction of an energy-saving device such as a multiple effect evaporator necessitates a cooler such as a chiller, which consumes a larger amount of power as compared to the other devices, if the temperature at the tower top is lower than or equal to 35° C., for example. However, since there is no need to condense the ethanol vapor in the present process, such a device can be eliminated.

Note that the ethanol vapor adiabatically compressed by the first compressor 86 may be introduced into the rectifying column 12 after being used as a heat source for the first superheater 85 provided at the previous stage of the first compressor 86. As a result, it is possible to prevent the condensation of the ethanol vapor in the first compressor 86. It is also possible to further reduce a consumption energy required in the vacuum distillation process P4.

Moreover, without providing the first superheater 85, the condensation of the ethanol vapor in the first compressor 86 may be prevented by recycling part of the ethanol vapor, which has been adiabatically compressed to increase the temperature and pressure thereof by means of the first compressor 86, to the entry side of the first compressor 86. Further, in a case where there is no possibility of generating the above-described problem due to the condensation, the distilled ethanol vapor may be directly compressed by the first compressor 86 without providing the first superheater 85 at the previous stage of the first compressor 86.

The ethanol vapor introduced into the rectifying column 12 and has a concentration of about 10% is separated into an ethanol liquid with an ethanol concentration of about 90% (90% ethanol liquid) and low COD drainage water. The 90% ethanol liquid is distilled from the tower top as ethanol vapor (the temperature thereof is about 79° C., for example). Note that the ethanol vapor distilled from the tower top is heat-exchanged with the tower bottom recycled liquid of the vacuum distillation tower 11 by means of the heat exchanger 80 so as to increase the temperature of the tower bottom recycled liquid as described above. Further, this ethanol vapor preheats the to ethanol-fermented 1 quid by means of a preheater 90. Thereafter, part of the ethanol vapor is sent to the dehydration process P6 through a distillation line 94. The remaining part of the ethanol vapor is recycled to the top of the rectifying column 12 as an ethanol reflux liquid through a reflux line 95 with a majority thereof being condensed.

The low COD drainage water is removed as a bottom product from the bottom of the rectifying column 12. Since this low COD drainage water is a distillate from the vacuum distillation tower 11, it contains no high-boiling component but contains only slight amounts of organic acid, oil, and the like. Therefore, it can be considered as colorless, transparent, and clean water although the COD of the low COD drainage water is about 1000 (mg/L). Thus, the recycled use of the low COD drainage water is possible in the pretreatment process P1, the saccharification process P2, or the solid-liquid separation process P7. Particularly in the solid-liquid separation process P7, the low COD drainage water is used as a rinse liquid. This low COD drainage water can also be treated by a drainage water treatment apparatus (not shown).

The low COD drainage water is sent out by a tower bottom recycling pump 93 and heat-exchanged with the tower bottom recycled liquid of the vacuum distillation tower 11 by the heat to exchanger 78 as described above. The low COD drainage water also preheats the ethanol-fermented liquid via a preheater 91.

Part of the low COD drainage water is subjected to temperature increase by a heat exchanger 92 using external vapor fed from the vapor line (not shown) or the like and recycled to the bottom of the rectifying column 12. Accordingly, the temperature at the tower bottom is 100° C., for example.

Although the heat exchange of the ethanol-fermented liquid is performed by the preheater 77, the preheater 90, and the preheater 91 arranged in parallel, these preheaters 77, 90, and 91 may be serially arranged or omitted in a case where the cost required for the branch of the ethanol-fermented liquid becomes excessive, or the like.

[Fifth Embodiment]

An apparatus for producing ethanol 97 according to the fifth embodiment of the present invention will now be described.

Note that an ethanol production process thereof is the same as that described in the first embodiment. Elements same as those in the first embodiment are denoted by the same reference numerals and the detailed description thereof will be omitted below.

Figure 6:
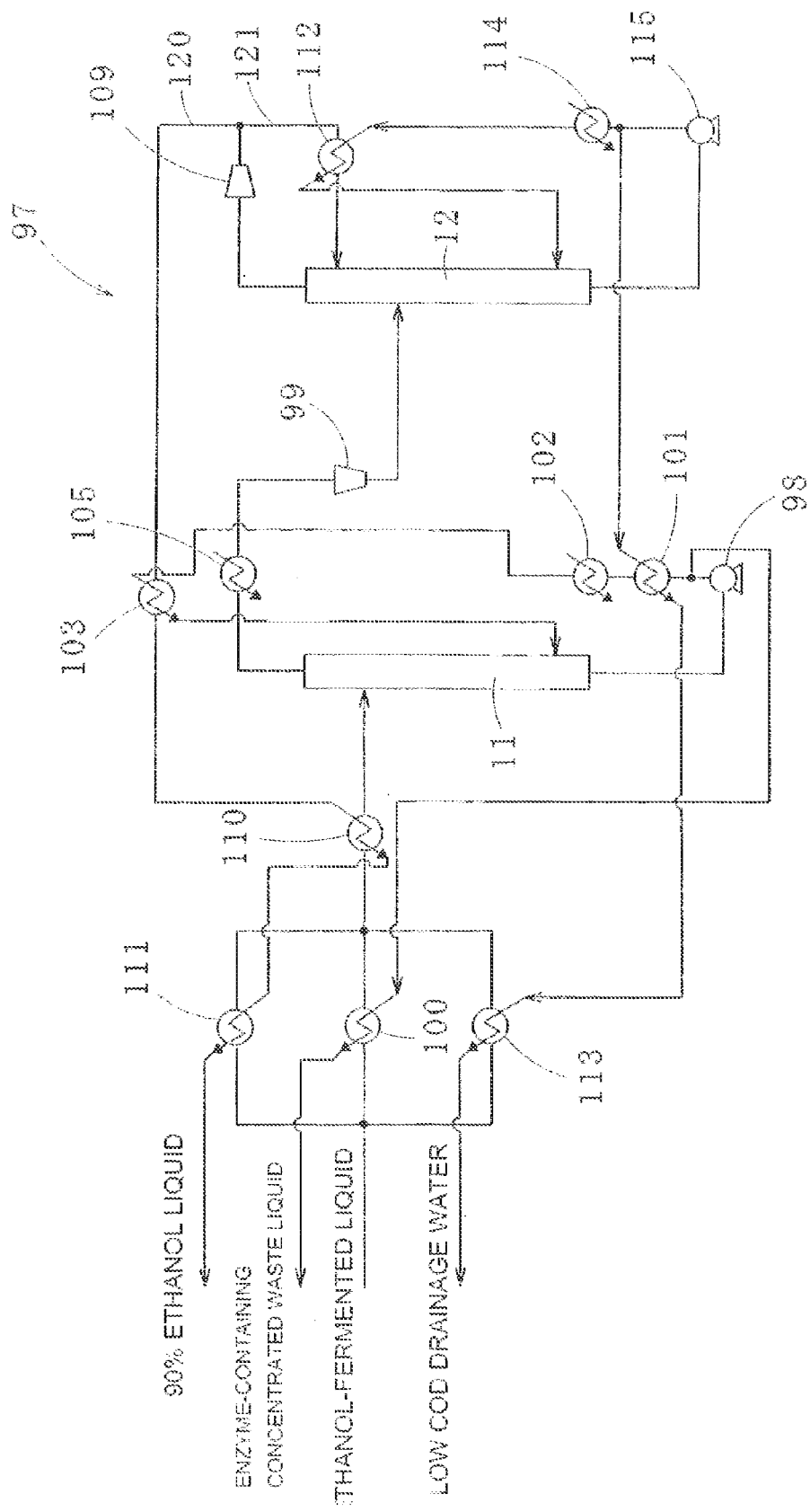
FIG. 6 is a configuration diagram of an apparatus for producing ethanol according to a fifth embodiment of the present invention.

As shown in FIG. 6, in the vacuum distillation process P4 and the rectifying process P5 of the apparatus for producing ethanol 97, distillation and rectification are performed by the vacuum distillation tower 11 and the rectifying column 12, respectively.

The ethanol-fermented liquid generated in the C6 sugar fermentation process P3 is introduced into the vacuum distillation tower 11. In order to prevent the deactivation of the diastatic enzyme, a first compressor 99 performs depressurization control so that the bottom temperature of the vacuum distillation tower 11 becomes a temperature higher than or equal to 30° C. and lower than 60° C. (preferably, in a range of 30° C. or higher and 51° C. or lower). The internal pressure of the vacuum distillation tower 11 is controlled to be 16 kPaA, for example.

The enzyme-containing concentrated waste liquid is removed as a bottom product from the bottom of the vacuum distillation tower 11. The enzyme-containing concentrated waste liquid removed as a bottom product is sent out by a tower bottom recycling pump 98, subjected to the solid-liquid separation process P7, and then reused in the fermenter in the C5 sugar fermentation process P8. Moreover, the enzyme-containing concentrated waste liquid preheats the ethanol-fermented liquid by means of a preheater 100.

Part of the enzyme-containing concentrated waste liquid removed as a bottom product from the bottom of the vacuum distillation tower 11 is subjected to temperature increase by means of a heat exchanger 101, a heat exchanger 102, and a heat exchanger 103 and then recycled into the bottom of the vacuum distillation tower 11 as a tower bottom recycled liquid. Note that the heat exchanger 101 employs, as a heat source, low COD drainage water (the temperature thereof is 100° C., for example) removed as a bottom product from the bottom of the rectifying column 12. The heat exchanger 102 performs a heat exchange with external vapor fed from a vapor line (not shown). The heat exchanger 103 performs a heat exchange with the ethanol vapor distilled from the top of the rectifying column 12. The bottom temperature of the vacuum distillation tower 11 is 45° C., for example.

Moreover, although the heat exchanger 101 and the heat exchanger 102 are placed outside the vacuum distillation tower 11, they may be integrated with the bottom portion of the vacuum distillation tower 11 so that a heat exchange can be conducted with vapor fed from the vapor line (not shown).

Ethanol vapor (the temperature thereof is 41° C., for example) is distilled from the top of the vacuum distillation tower 11. The amount of this ethanol vapor is determined by the amount of the enzyme-containing concentrated waste liquid which can be recycled over the entire ethanol production process. The following methods, for example, can be conceived in order to control this recycled amount of the enzyme-containing concentrated waste liquid. As a first example, in order to maintain a fixed level in a buffer tank of a C5 sugar-fermented liquid, the control therefor can be made by altering a supplied amount of vapor in the vacuum distillation process P4, the number of revolutions in the first compressor 99, or an amount of the ethanol vapor distilled from the vacuum distillation tower 11. As a second example, refractivity (sugar concentration) of the enzyme-containing concentrated waste liquid is measured by means of a refractometer (Brix meter). In order to maintain this measured value constant, the control therefor can be made by altering a supplied amount of vapor in the vacuum distillation process P4, the number of revolutions in the first compressor 99, or an amount of the ethanol vapor distilled from the vacuum distillation tower 11.

The ethanol vapor distilled from the top of the vacuum distillation tower 11 is heated by a first superheater 105, which employs vapor fed from the vapor line (not shown) as a heat source, so as to prevent the condensation thereof while being delivered to the rectifying column 12. Here in general, if the ethanol vapor distilled from the tower top is condensed while being delivered to the rectifying column 12, a mechanical problem may occur, for example, an excessive load may be imposed on a rotating part such as an impeller (a vane part) within the first compressor 99, the condensed liquid may be leaked from a sealing portion, or the like. In the present embodiment, since the ethanol vapor distilled from the top of the vacuum distillation tower 11 is heated by the first superheater 105, it is possible to prevent the occurrence of the problem caused by such condensation.

Further, the heated ethanol vapor is adiabatically compressed, and the temperature thereof and the pressure thereof are thus increased by the first compressor 99. Thereafter, the ethanol vapor is introduced into the rectifying column 12.

Thus, since the ethanol vapor is introduced into the rectifying column 12 as vapor without being cooled and condensed as in a conventional technique, an energy required for the operation of the rectifying column 12 is reduced. Further, the introduction of an energy-saving device such as a multiple-effect evaporator necessitates a cooler such as a chiller, which consumes a larger amount of power as compared to a conventionally-employed cooling tower, if the temperature at the tower top is lower than or equal to 35° C., for example. However, since there is no need to condense the ethanol vapor in the present process, such a device can be eliminated.

Note that the ethanol vapor adiabatically compressed by the first compressor 99 may be introduced into the rectifying column 12 after being used as a hear source for the first superheater 105 provided at the previous stage of the first compressor 99. As a result, it is possible to prevent the condensation of the ethanol vapor in the first compressor 99. It is also possible to further reduce a consumption energy required in the vacuum distillation process P4.

Moreover, without providing the first superheater 105, the condensation of the ethanol vapor in the compressor may be prevented by recycling part of the ethanol vapor, which has been subjected to the adiabatic compression to increase the temperature thereof by means of the compressor, to the entry side of the first compressor 99. Further, in a case where there is no possibility of generating the above-described problem due to the condensation, the distilled ethanol vapor may be directly compressed by the first compressor 99 without providing the first superheater 105 at the previous stage of the first compressor 99.

The ethanol vapor introduced into the rectifying column 12 and having a concentration of about 10% is separated into an ethanol liquid with an ethanol concentration of about 90% (90% ethanol liquid) and low COD drainage water. The 90% ethanol liquid is distilled from the tower top as ethanol vapor (the temperature thereof is about 79° C., for example) and compressed by a second compressor 109. Part of the compressed to ethanol vapor is sent to the dehydration process P6 through a distillation line 120. Note that the part of the ethanol vapor distilled from the tower top is heat-exchanged with the tower bottom recycled liquid of the vacuum distillation tower 11 by means of the heat exchanger 103 as described above. Further, this ethanol vapor preheats the ethanol-fermented liquid by means of a preheater 110 and a preheater 111.

Note that the ethanol vapor distilled from the tower top is compressed by the second compressor 109, and part of the compressed ethanol vapor is passed through a heat exchanger 112 using a reflux line 121 and recycled to the top of the rectifying column 12 as an ethanol reflux liquid with a majority thereof being condensed.

The low COD drainage water is removed as a bottom product from the bottom of the rectifying column 12. Since this low COD drainage water is a distillate from the vacuum distillation tower 11, it contains no high-boiling component but contains only slight amounts of organic acid, oil, and the like. Therefore, it can be considered as colorless, transparent, and clean water although the COD of the low COD drainage water is about 1000 (mg/L). Thus, the recycled use of the low COD drainage water is possible in the pretreatment process P1, the saccharification process P2, or the solid-liquid separation process P7. Particularly in the solid-liquid separation process P7, the low COD drainage water is used as a rinse liquid. This low COD drainage water can also be treated by a drainage water treatment apparatus (not shown).

The low COD drainage water is sent out by a tower bottom recycling pump 115 and heat-exchanged with the tower bottom recycled liquid of the vacuum distillation tower 11 by the heat exchanger 101 as described above. The low COD drainage water also preheats the ethanol-fermented liquid via a preheater 113.

Part of the low COD drainage water is subjected to temperature increase by means of a heat exchanger 114 and the heat exchanger 112 and recycled to the bottom of the rectifying column 12. The heat exchanger 114 performs a heat exchange with external vapor fed from the vapor line (not shown). Note that the heat source for the heat exchanger 112 is the ethanol vapor which has been compressed to increase the temperature and pressure thereof by means of the second compressor 109 as described above. Accordingly, the temperature at the tower bottom is 100° C., for example.

Although the heat exchange of the ethanol-fermented liquid is performed by the preheater 100, the preheater 111, and the preheater 113 arranged in parallel, these preheaters 100, 111, and 113 may be serially arranged. The ethanol vapor compressed by the second compressor 109 can also be employed as a heat source for the first superheater 105.

The present inventor conducted trial calculation on the effects of energy reduction by the above-described ethanol production apparatuses according to the first to fifth is embodiments. The results are shown in Table 1.

TABLE 1

| | | BASE DATA | COMPARATIVE EXAMPLE 1 WITHOUT COMPRESSOR | COMPARATIVE EXAMPLE 2 COMBINATION OF MULTIPLE-EFFECT EVAPORATOR AND CHILLER | FIRST EMBODIMENT FIG. 2 | SECOND EMBODIMENT FIG. 3 | THIRD EMBODIMENT FIG. 4 | FOURTH EMBODIMENT FIG. 5 | FIFTH EMBODIMENT FIG. 6 |
|---|---|---|---|---|---|---|---|---|---|
| VACUUM VAPOR[1] (Mcal) | A1 | 900 | 900 | 300 | 900 | 0 | 0 | 700 | 850 |
| VACUUM COMPRESSION[2] (Mcal) | B1 | 60 | 0 | 0 | 60 | 60 | 60 | 60 | 60 |
| CHILLER POWER[3] (Mcal) | B2 | — | 0 | 167 | 0 | 0 | 0 | 0 | 0 |
| ATMOSPHERIC VAPOR[4] (Mcal) | A2 | 350 | 350 | 350 | 35 | 0 | 0 | 35 | 0 |
| ATMOSPHERIC COMPRESSION[5] (Mcal) | B3 | 50 | 0 | 0 | 0 | 53 | 50 | 0 | 50 |
| TOTAL VAPOR (Mcal) | C = A1 + A2 | — | 1250 | 650 | 935 | 0 | 0 | 735 | 850 |
| TOTAL POWER (Mcal) | D = B1 + B2 + B3 | — | 0 | 167 | 60 | 113 | 110 | 60 | 110 |
| TOTAL IN VAPOR EQUIVALENT (Mcal) | E = C + D × 3 | — | 1250 | 1151 | 1115 | 339 | 330 | 915 | 1180 |
| ENERGY COMPARISON | — | — | 100 | 92 | 89 | 27 | 26 | 73 | 94 |

[1]EXTERNAL ENERGY REQUIRED FOR DISTILLATION OF VACCUM DISTILLATION TOWER 11
[2]ENERGY REQUIRED FOR COMPRESSION OF COMPRESSOR (16, 242, 42, 86, OR 99)
[3]ENERGY REQUIRED FOR OPERATION OF CHILLER
[4]EXTERNAL ENERGY REQUIRED FOR RECTIFICATION OF RECTIFYING COLUMN 12
[5]ENERGY REQUIRED FOR COMPRESSION OF COMPRESSOR (262, 62, OR 109)

Note that the starting material is a wooden chip. The calculation conditions are as follows.

<Calculation Conditions>
1. Ethanol-fermented liquid: 10,484 kg/h (ethanol concentration of 3%)
2. Enzyme-containing concentrated waste liquid: 8,737 kg/h
3. Ethanol distilled from vacuum distillation tower: 1,747 kg/h (ethanol concentration of 14%) (=ethanol-fermented liquid 10,484 kg/h—enzyme-containing concentrated waste liquid 8,737 kg/h)
4. Low COD drainage water: 1,476 kg/h (=ethanol distilled from vacuum distillation tower 1,747 kg/h-90% ethanol 271 kg/h)
5. 90% ethanol: 271 kg/h (244 kg/h/90 wt %)
6. Reflux ratio about rectification: 3

Upon the trial calculation, conversion was made with the electric energy corresponding to ⅓ of the vapor energy. The amount of vapor use for the multiple-effect was set to ⅓ of that for typical distillation assuming that it is triple effect. The COP (Coefficient Of Performance) of the chiller was set to 1.8. The adiabatic compression efficiency of the compressor was 50%.

Note that in the first and fourth embodiments, atmospheric vapor (external vapor) can be reduced to 35, which is about ¹⁄₁₀ of the typical amount, as a supplemental energy. This is because the energy required for the rectifying column 12 is covered almost entirely by the ethanol vapor introduced into the rectifying column 12 after the temperature and pressure thereof are increased by the compressor 16 (86).

Moreover, in the fourth embodiment, the vacuum vapor can be reduced to 700. (An energy of 200 is used from among an energy of 350 introduced at the tower bottom.) This is because the energy required for the vacuum distillation tower 11 utilizes the energy of latent heat retained by the ethanol vapor at the top of the rectifying column 12.

Moreover, in the fifth embodiment, the vacuum vapor can be reduced to 850.

This is because the energy required for the vacuum distillation cower 11 utilizes the energy of latent heat and sensible heat retained by part of the ethanol vapor at the top of the rectifying column 12.

In Table 1, Comparative Example 1 shows a trial calculation result in a case where distillation is performed simply by vapor only without providing a multiple-effect evaporator or the like. This result was set to 100 as a reference.

Comparative Example 2 shows a trial calculation result in a case where distillation is performed in combination of a multiple-effect evaporator and a chiller. Regarding Comparative Example 2, the chiller is required since the temperature at the tower top becomes lower than or equal to 35° C. Thus, the required external energy is 92 in vapor equivalent.

1) Regarding the First Embodiment

As shown in FIG. 2, by introducing the ethanol vapor distilled from the vacuum distillation tower 11, which has been subjected to temperature increase and pressure increase by the it first compressor 16 without being condensed, into the rectifying column 12, the external energy can be reduced to 89 in vapor equivalent.

2) Regarding the Second Embodiment

As shown in FIG. 3, the ethanol vapor distilled from the vacuum distillation tower 11 is utilized as a heat source for the vacuum distillation tower 11 after being subjected to temperature increase and pressure increase by the first compressor 242 without being condensed, and also the ethanol vapor distilled from the rectifying column 12 is utilized as a heat source for the rectifying column 12 without being condensed. As a result, the external energy can be reduced to 27 in vapor equivalent.

3) Regarding the Third Embodiment

As shown in FIG. 4, the ethanol vapor distilled from the vacuum distillation tower 11 is utilized as a heat source for the vacuum distillation tower 11 after being subjected to temperature increase and pressure increase by the first compressor 42 without being condensed, and the ethanol vapor distilled from the rectifying column 12 is also utilized as a heat source for the rectifying column 12 without being condensed. As a result, the external energy can be reduced to 26 in vapor equivalent.

4) Regarding the Fourth Embodiment

As shown in FIG. 5, the ethanol vapor distilled from the vacuum distillation tower 11 is introduced into the rectifying column 12 without being condensed, and the ethanol vapor distilled from the rectifying column 12 is utilized as a heat source for the vacuum distillation tower 11. As a result, the external energy can be reduced to 73 in vapor equivalent.

5) Regarding the Fifth Embodiment

As shown in FIG. 6, the ethanol vapor distilled from the vacuum distillation tower 11 is introduced into the rectifying column 12 without being condensed, and the ethanol vapor distilled from the rectifying column 12 is utilized as a heat source for the rectifying column 12 without being condensed. As a result, the external energy can be reduced to 94 in vapor equivalent.

In view of the above, it is possible in any of the embodiments to realize a more efficient use of the energy of the ethanol vapor at the exit side of the first compressor, which corresponds to the largest energy. Note however that the third embodiment can be considered as an embodiment realizing the most efficient use of the energy of the ethanol vapor among these embodiments.

It is to be understood that the present invention is not limited to the embodiments described above, and any change is possible unless it changes the gist of the present invention. For example, a case where the present invention is constructed by combining together a part or all of the above-described embodiments and modifications thereof is also included in the technical scope of the present invention.

The vacuum distillation tower 11 in the above-described embodiments may be a vacuum concentrating device for concentrating the ethanol-fermented liquid. Moreover, the first compressor in the above-described embodiments may be a blower or a vacuum pump. Further, the second compressor in the above-described embodiments may be a blower or a vacuum pump.

REFERENCE SIGNS LIST

10: apparatus for producing ethanol, 11: vacuum distillation tower, 12: rectifying column, 15: tower bottom recycling pump, 16: first compressor, 17: heat exchanger, 18: first superheater, 20: cooler, 21: heat exchanger, 22: tower bottom recycling pump, 30: apparatus for producing ethanol, 31: tower bottom recycling pump, 32: preheater, 33: heat exchanger, 34: heat exchanger, 41: first superheater, 42: first compressor, 51: tower bottom recycling pump, 52: preheater, 53: preheater, 54: heat exchanger, 61: second super heater, 62: second compressor, 63: preheater, 64: preheater, 65: preheater, 66: preheater, 67: reflux line, 68: distillation line, 70: apparatus for producing ethanol, 75: tower bottom recycling pump, 77: preheater, 78: heat exchanger, 79: heat exchanger, 80: heat exchanger, 85: first superheater, 86: first compressor, 90: preheater, 91: preheater, 92: heat exchanger, 93: tower bottom recycling pump, 94: distillation line, 95: reflux line, 97 apparatus for producing ethanol, 98: tower bottom recycling pump, 99: first compressor, 100: preheater, 101: heat exchanger, 102: heat exchanger, 103: heat exchanger, 105: first superheater, 109: second compressor, 110: preheater, 111: preheater, 112: heat exchanger, 113: preheater, 114: heat exchanger, 115: tower bottom recycling pump, 120: distillation line, 121: reflux line, 200: apparatus for producing ethanol, 231: tower bottom recycling pump, 232: preheater, 234: heat exchanger, 241: first superheater, 242: first compressor, 251: tower bottom recycling pump, 252: preheater, 254: heat exchanger, 261: second superheater, 262: second compressor, 264: preheater, 265: preheater, 267: reflux line, 268: distillation line

The invention claimed is:

1. A method for producing ethanol by purifying ethanol from an ethanol-fermented liquid containing a diastatic enzyme and 1 to 10% ethanol generated by saccharification fermentation of a pretreated biomass starting material, the method comprising:
   a step of pretreating a biomass starting material to enhance enzyme reactivity to form a pretreated biomass starting material comprising pulp;
   a step of subjecting the pretreated biomass starting material to saccharification fermentation to form the ethanol-fermented liquid;
   a step of subjecting the ethanol-fermented liquid containing the diastatic enzyme and 1 to 10% ethanol to vacuum distillation to produce an ethanol vapor containing water vapor and an enzyme-containing concentrated waste liquid;
   a step of adiabatically compressing the ethanol vapor to increase the temperature and the pressure of the ethanol vapor;
   a step of rectifying the ethanol vapor; and
   a step of recycling the enzyme-containing concentrated waste liquid to a step of subjecting the pretreated biomass starting material to saccharification fermentation,
   wherein the method further comprises a step of adjusting a flow rate of the ethanol vapor from the step of subjecting the ethanol-fermented liquid to vacuum distillation to produce ethanol vapor containing water vapor and the enzyme-containing concentrated waste liquid so that a weight of the enzyme-containing concentrated waste liquid from the step of subjecting the ethanol-fermented liquid to vacuum distillation to produce ethanol vapor containing water vapor and the enzyme-containing concentrated waste liquid becomes 2 to 20 times as much as a pulp weight generated in the pretreatment for enhancing an enzyme reactivity of the biomass starting material.

2. The method for producing ethanol according to claim 1, further comprising a step of heat-exchanging the ethanol vapor having been subjected to temperature increase and pressure increase by the step of adiabatically compressing the ethanol vapor with a tower bottom recycled liquid of a vacuum distillation tower to achieve condensation thereof, and wherein
   the ethanol vapor from the vacuum distillation tower is introduced into the rectifying step after the ethanol vapor is converted into an ethanol liquid.

3. The method for producing ethanol according to claim 1, wherein a part of the ethanol vapor adiabatically compressed by a first compressor used in the step of adiabatically compressing the ethanol vapor is recycled to an entry side of the first compressor.

* * * * *